(12) United States Patent
Abdelgany et al.

(10) Patent No.: US 7,988,625 B2
(45) Date of Patent: Aug. 2, 2011

(54) SURGICAL RETRACTOR WITH REMOVABLE SCISSOR ARMS

(75) Inventors: Mahmoud F. Abdelgany, Rockaway, NJ (US); Gregory Martin, New York, NY (US)

(73) Assignee: Stryker Spine (FR)

( * ) Notice: Subject to any disclaimer, the term of this patent is extended or adjusted under 35 U.S.C. 154(b) by 1207 days.

(21) Appl. No.: 11/652,810

(22) Filed: Jan. 12, 2007

(65) Prior Publication Data
US 2007/0123753 A1    May 31, 2007

Related U.S. Application Data

(62) Division of application No. 10/943,520, filed on Sep. 17, 2004, now Pat. No. 7,182,729.

(60) Provisional application No. 60/503,944, filed on Sep. 18, 2003, provisional application No. 60/519,202, filed on Nov. 12, 2003.

(51) Int. Cl.
*A61B 1/32* (2006.01)

(52) U.S. Cl. ...................................... 600/220

(58) Field of Classification Search ............ 600/201, 600/203, 208, 210, 213, 214, 215, 219, 220, 600/221, 222, 225, 226, 227, 228; 606/119
See application file for complete search history.

(56) References Cited

U.S. PATENT DOCUMENTS

| | | | |
|---|---|---|---|
| 430,350 A | 6/1890 | McCully | |
| 1,275,520 A | 8/1918 | Bell | |
| 1,919,120 A | 7/1933 | O'Connor et al. | |
| 2,083,573 A | 6/1937 | Morgan | |
| 3,030,947 A | 4/1962 | Engelbert | |
| 3,044,461 A | 7/1962 | Murdock | |
| 4,263,899 A | 4/1981 | Burgin | |
| 4,597,383 A | 7/1986 | VanDerBel | |
| 5,007,409 A | 4/1991 | Pope | |
| 5,178,133 A | 1/1993 | Pena | |
| 5,503,617 A | 4/1996 | Jako | |
| 5,667,520 A | 9/1997 | Bonutti | |
| 5,681,340 A | 10/1997 | Veronikis | |
| 5,755,661 A | 5/1998 | Schwartzman | |
| 5,792,044 A | 8/1998 | Foley et al. | |
| 5,795,291 A | 8/1998 | Koros et al. | |
| 5,813,978 A | 9/1998 | Jako | |
| 5,879,291 A | 3/1999 | Kolata et al. | |
| 5,944,658 A | 8/1999 | Koros et al. | |
| 5,976,146 A | 11/1999 | Ogawa et al. | |
| 6,036,638 A | 3/2000 | Nwawka | |
| 6,083,154 A | 7/2000 | Liu et al. | |
| 6,099,547 A | 8/2000 | Gellman et al. | |
| 6,187,000 B1 | 2/2001 | Davison et al. | |

(Continued)

FOREIGN PATENT DOCUMENTS

DE    197 40 576 A1    4/1999

(Continued)

*Primary Examiner* — Eduardo C Robert
*Assistant Examiner* — David Comstock
(74) *Attorney, Agent, or Firm* — Lerner, David, Littenberg, Krumholz & Mentlik, LLP

(57) ABSTRACT

A retractor having interchangeable or replaceable blades facilitates the expansion of a surgical site below an incision in the skin, and establishes a work-through surgical space. The retractor includes a frame connected to two collar arms, a pair of blades connected to the collar arms, a sheath for encompassing the blades and providing a circumscribed working space, and a device for rotating the collar arms, thereby displacing the blades and any tissue surrounding them.

19 Claims, 4 Drawing Sheets

U.S. PATENT DOCUMENTS

| | | |
|---|---|---|
| 6,224,545 B1 | 5/2001 | Cocchia et al. |
| 6,371,968 B1 | 4/2002 | Kogasaka et al. |
| 6,432,048 B1 | 8/2002 | Francois |
| 6,524,320 B2 | 2/2003 | DiPoto |
| 7,182,729 B2 * | 2/2007 | Abdelgany et al. ........... 600/219 |
| 2002/0183595 A1 | 12/2002 | Rioux et al. |
| 2003/0069477 A1 | 4/2003 | Raisman et al. |
| 2003/0149341 A1 | 8/2003 | Clifton |
| 2003/0191371 A1 | 10/2003 | Smith et al. |
| 2004/0002629 A1 | 1/2004 | Branch et al. |

FOREIGN PATENT DOCUMENTS

| | | |
|---|---|---|
| EP | 0 890 341 | 6/1908 |
| EP | 0 455 282 B1 | 11/1991 |
| EP | 0 614 646 A1 | 9/1994 |
| EP | 1 036 544 A1 | 9/2000 |
| WO | WO-94/21179 | 9/1994 |
| WO | WO-2004/062489 A1 | 7/2004 |

* cited by examiner

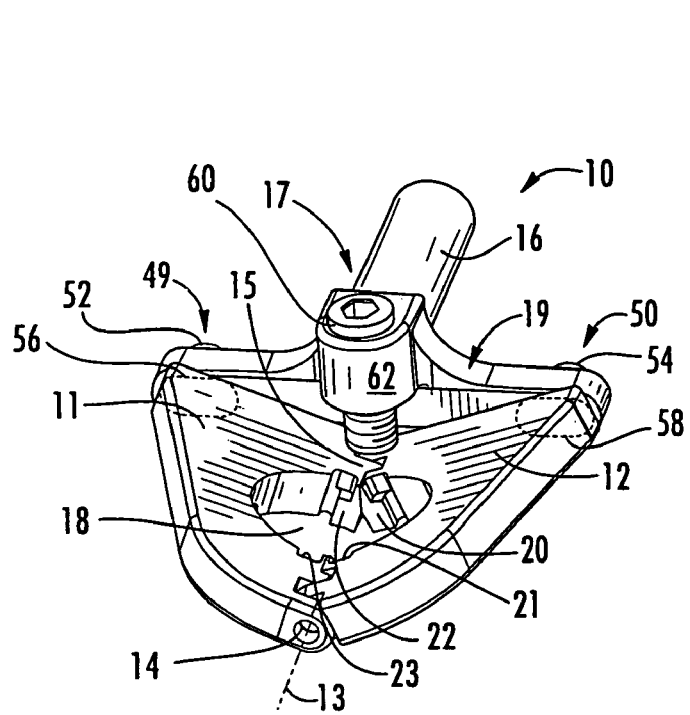

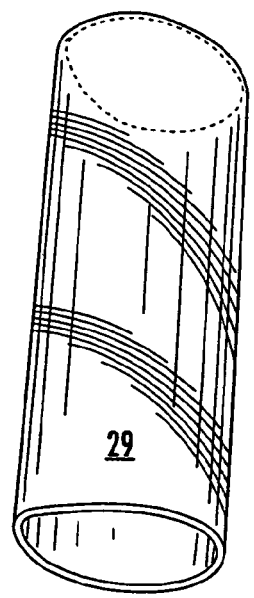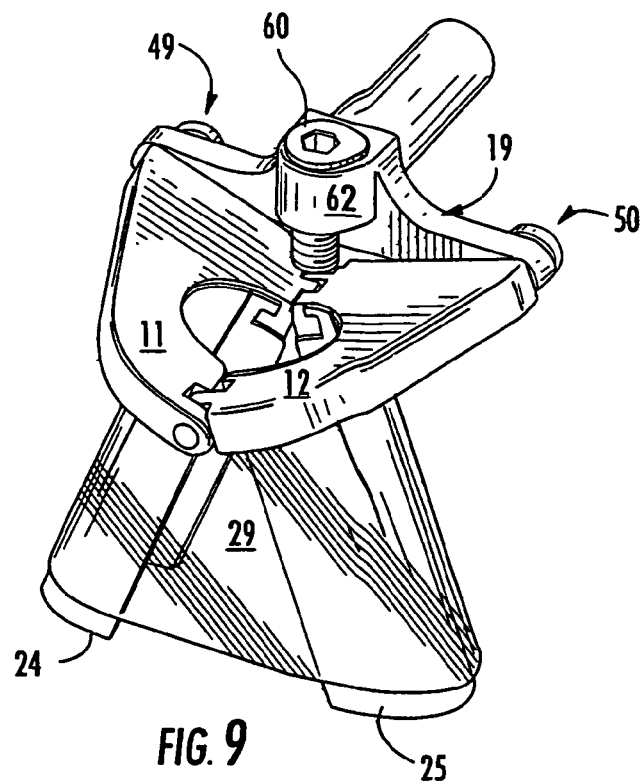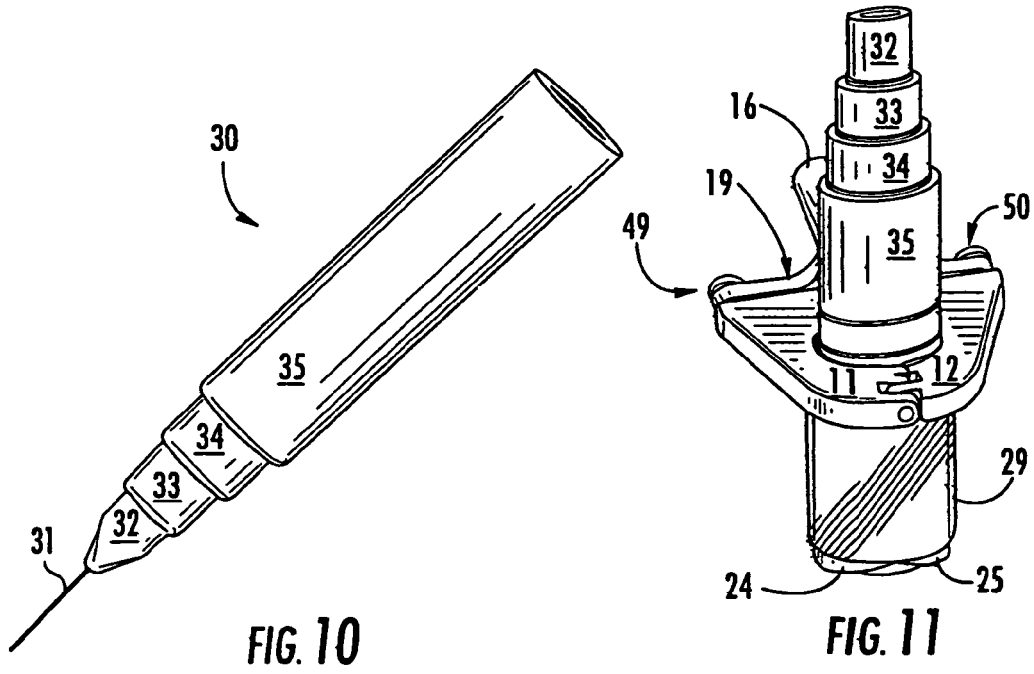

SURGICAL RETRACTOR WITH REMOVABLE SCISSOR ARMS

CROSS-REFERENCE TO RELATED APPLICATION

This application is a divisional, of U.S. application Ser. No. 10/943,520, filed on Sep. 17, 2004, the disclosure of which is incorporated herein by reference. This application claims the benefit of the filing date of U.S. Provisional Application No. 60/503,944, filed Sep. 18, 2003, and U.S. Provisional Application No. 60/519,202, filed Nov. 12, 2003, the disclosures of which are hereby incorporated herein by reference.

BACKGROUND OF THE INVENTION

The present invention relates to a device used to retract tissue within the body of a patient. More specifically, the present invention relates to a retractor that facilitates enlarging a surgical cavity and providing a work-through channel to the surgical site.

Since it is advantageous to perform surgery in ways that minimize tissue trauma, the present minimally invasive approach facilitates a smaller incision, less tissue trauma, and faster patient rehabilitation, as compared to traditional incision and retraction techniques.

The various embodiments of the present invention are particularly useful for orthopedic surgery of the spine, but are envisioned to be limitlessly applicable to other surgical techniques and other parts of the body.

SUMMARY OF THE INVENTION

An aspect of the present invention provides an apparatus for conducting a less invasive surgical procedure by making a relatively small incision in a patient's skin and forming a larger surgical cavity below the incision. The surgical retractor according to this aspect of the invention includes a mount having a frame connected through two translating pivot points to two collar arms, where the two collar arms are attached together at least one hinge, a pair of blades connected to the collar arms, and an actuator for rotating the two collar arms along the hinge axis, thereby displacing the blades. Preferably, the actuator is located close to the hinge connecting the collar arms, and is not a separate instrument. Also preferably, the actuator is at an angle relative to the frame in order to provide clearance with the patient's skin when the axis of the retractor is not perpendicular to the skin. Another aspect of the present invention provides that at least a portion of the actuator is part of the frame.

One aspect of the actuator includes a screw threadably associated with a housing that is part of the frame. In this aspect, when the screw is turned, or actuated, it moves distally and bears on both collar arms, thus pushing them downwardly and forcing the blades to open.

Another preferred aspect of the actuator further includes a ball in communication with the screw and in communication with a hinge pin linking the collar arms together. Optionally, a guide may be attached to the pin, wherein the guide provides a contact surface for the ball. Thus, when the screw is turned, it translates and bears on the ball, which itself moves and bears on the guide, which, because of its connection to the hinge pin, forces the hinge pin and hinge of the two collar arms to move distally, thereby pushing both collar arms downwardly and forcing the blades to open.

Yet another preferred aspect of the invention includes a tool, such as a screwdriver or an Allan key, that engages the actuator to move the actuator and thus cause the blades to move, either to separate or to come together.

In yet another aspect, the mount is preferably situated above the skin of the patient and has an opening therethrough allowing entry into the surgical cavity.

Another aspect of the present invention provides a mount comprising two collar arms attached at two hinge points. The mount includes an opening through its center leading to a channel, whereby a portion of the opening resides on each of the two collar arms. In a preferred embodiment, the opening is of an oval cross-section. However, this opening can be of any diameter, shape, or cross-sectional area. Additionally, the mount can be of any size or shape and the opening in the mount may or may not correspond to the shape of the tube created by the blades that are attached to the collar arms.

Another aspect of the present invention further provides blades having a shape and a length. In a preferred embodiment, the blades are curved, whereby together, they form an oval tube when in a non-expanded position. Upon rotation of the collar arms, the blades move outwardly, thereby displacing tissue and enlarging the surgical cavity. The major and minor diameters of the oval tube can be of any size. It should be noted that the blades can be of any shape and may or may not correspond to the shape of the mount. For example, the curvature of the blade may differ from that of the opening. Similarly, the blades can be of any length thereby creating surgical cavities with different depths. Additionally, the blades have tapered ends which facilitate progressive tissue penetration. This allows for improved control during insertion and less damage to the tissue.

Another aspect of the present invention further provides blades that are easily detachable from the mount. In a preferred embodiment, the blades are attached to the mount through the use of male and female connectors. These connectors facilitate easily attaching and detaching the blades from the mount. The blades may be attached by compressing them to fit within the opening, and then allowing them to spring back to original shape and engage the respective connectors. Detachment may be similarly achieved by compressing the blades to disassociate the respective connectors, thereby freeing the blades for removal and/or replacement. Other connection configurations are also envisioned.

The blades may be constructed of any sturdy material, and preferably from a radiolucent or semi-radiolucent material. In a preferred embodiment, thin, semi-radiolucent aluminum is employed. This allows for improved visualization of the surgical site when viewed on an X-ray with the retractor in place. In another embodiment, a non-autoclavable or non-sterilizable material may also be utilized.

The blades, as well as the collar, may also be constructed of a light-conducting material, such as acrylic, for example. Preferably a cable transfers light from a light source to the collar and blades, which then illuminate the working space.

It is also contemplated, in a preferred embodiment, that the blades are easily interchangeable. This allows for quick changes in length, depth, or shape of the blades depending upon a particular surgical situation. Thus, among other advantages, the desired length, depth, or shape of blades can be changed without having to utilize an entirely new device.

In another preferred embodiment, the blades can be disposable, either in addition to the interchangeable feature, or independent of that feature. In this regard, in a preferred embodiment, the blades may be removable for disposability, or the blades and the collar to which they are connected may be disposable. Preferred methods contemplate the interchangeability, illumination and/or the disposability features in various forms.

Another aspect of the present invention further provides a sheath that covers the blades. The sheath expands when the blades are extended outwardly thereby creating an enlarged surgical cavity that is enclosed by the retractor and sheath. The sheath also contracts along with the inward retraction of the blades. In a preferred embodiment, the sheath is constructed of pliable elastic material, such as silicone rubber, thereby allowing for both its expansion and contraction. It is envisioned that the sheath can be made of any material and can be any length, thickness, or shape, as well as transparency or opaqueness. In a preferred embodiment, the sheath fits snuggly over the blades in both the retracted and expanded positions. The sheath material can be such that it facilitates easy assembly onto, and removal from, the blades. The sheath may also be disposable, and a preferred method contemplates such disposability. Additionally, the sheath may cover any portion of the blades up to and including their entire surface area.

Another aspect of the present invention provides a bar for use with the retractor. The bar can be easily attached to a rigid, relatively fixed object on a first end and to the retractor on a second end. The bar is used to hold the retractor in position relative to the patient. Multiple bars may also be interconnected, thus forming a support assembly, to allow for discreet positioning of two or more retractors relative to each other. One example of a support assembly is the AF400 SpineTract System manufactured by Omni-Tract Surgical, a division of Minnesota Scientific. However, any type of bar or assembly can be used.

Another aspect of the present invention provides an apparatus for dilating an opening created by a small incision in the skin of a patient. The apparatus according to this aspect of the invention includes a guide and a variable number of dilators, whereby the first dilator fit over the guide and subsequent dilators of increasing size are sequentially fit over one another. In a preferred embodiment, the dilators are oval tubes having major and minor inside and outside diameters. Increasingly sized dilators are configured such that each larger dilator can fit over a smaller dilator. In a preferred method, the guide is inserted in an incision in the skin of the patient. Then a first dilator is moved down the guide thereby increasing the size of the surgical cavity. The first dilator has outside major and minor diameters which are slightly smaller than the inside major and minor diameters of the second dilator. The second dilator is then slid over the first dilator, thereby once again increasing the size of the surgical cavity. These steps are repeated until the desired surgical cavity size is achieved with a corresponding sized dilator, at which point the retractor, it its closed form, may be inserted into the surgical cavity over the largest dilator, the dilators removed therefrom, and the retractor expanded to further enlarge the surgical cavity below the incision.

Yet another aspect of the present invention further provides a surgical retractor having a mount and blades as described previously. With the mount in an unexpanded state, the blades form a tube having an opening extending through the mount. This tube has an inside cross-sectional shape larger than that of the largest dilator. This allows for the retractor to be placed over the largest dilator and into the enlarged surgical cavity. In a preferred embodiment, the opening in the mount, the tube formed by the blades of the retractor, and the dilators are all of an oval cross-sectional configuration. However, it is recognized that other shapes and sizes are possible.

Another aspect of the present invention provides for a method of creating a larger surgical cavity through a smaller incision in the skin of a patient. A preferred method includes making an incision in the skin of a patient, securing the guide to a portion of the patient, moving a first smaller sized dilator over the guide to expand tissue, adding further increasingly sized dilators over one another and progressively dilating the incision until the desired surgical cavity size is achieved with a correspondingly sized dilator, sliding the retractor over the largest inserted dilator, removing all of the dilators through the retractor, and by using the actuator, rotating the two collar arms of the mount along the hinge axis thereby displacing the blades laterally and moving the patient's tissue to enlarge a surgical cavity. Alternatively, the guide, and all but the largest dilator, may first be removed from the cavity prior to insertion of the retractor. The amount of rotation of the collar arms of the mount along the hinge axis determines the enlargement of the surgical cavity.

Another aspect of the present invention further provides for a method wherein the blades of the retractor are first covered with a sheath before they are introduced into the body of the patient. The sheath, as discussed previously, allows the retractor to form a surgical cavity enclosed by the apparatus. This, in turn, allows for better use of the surgical cavity as surrounding tissue can be prevented from entering the cavity. It is also noted that the sheath may be transparent thus allowing visualization of the expanded cavity outside of the sheath.

Another aspect of the present invention further provides for a method wherein, prior to displacing the blades of the retractor, a rod is connected to a rigid, relatively fixed object on the rod's first end, and to the retractor on the rod's second end. This step allows for enhanced control of the retractor before and after it is inserted into the body of the patient.

Another aspect of the present invention further provides that the retractor be inserted into the body of a patient so that the blades of the retractor displace in the same direction in which the muscles run in the area of the incision. This step facilitates minimizing the amount of damage to the muscle tissue upon the expansion of the blades of the retractor.

Yet another aspect of the present invention further provides for a method for creating a surgical cavity in a body wherein, various elements of the present retractor or the entire retractor, are disposable. In a preferred embodiment, additional steps of removing the retractor and disposing of the entire apparatus are performed. In another embodiment, additional steps of removing the retractor and disposing of a portion of it, for example, the blades are performed. In yet another embodiment, additional steps of sterilizing a portion of the retractor and attaching a non-autoclavable, or otherwise non-sterilizable portion, to the sterilized portion are performed. Subsequent to use of the retractor, the non-autoclavable, or otherwise non-sterilizable portion can be disposed.

Another aspect of the present invention provides for a kit including the various elements of the present invention. The kit comprises differently sized and shaped mounts, blades, and sheaths. The different elements may be interchanged to conform to the given surgical situation. In another embodiment, a method is contemplated wherein elements of desired shape and size are selected and connected to one another to provide a retractor best suited to create the proper surgical cavity.

BRIEF DESCRIPTION OF THE DRAWINGS

FIG. 1 is a perspective view of one embodiment of the mount portion of the retractor;
FIG. 2 is a perspective view of a blade of the retractor;
FIG. 3 is a side view of the blade of FIG. 2;
FIG. 4 is a view of the inside of the blade of FIG. 2;
FIG. 5 is a top view of the blade of FIG. 2;

FIG. 8 is a perspective view of a sheath;

FIG. 9 is a perspective view of the retractor in the open position with a sheath around the displaced blades;

FIG. 10 is a perspective view of a dilator assembly;

FIG. 11 is a perspective view of a retractor in the closed position with a sheath around the blades, placed over the dilator assembly.

DETAILED DESCRIPTION

Figure 6:
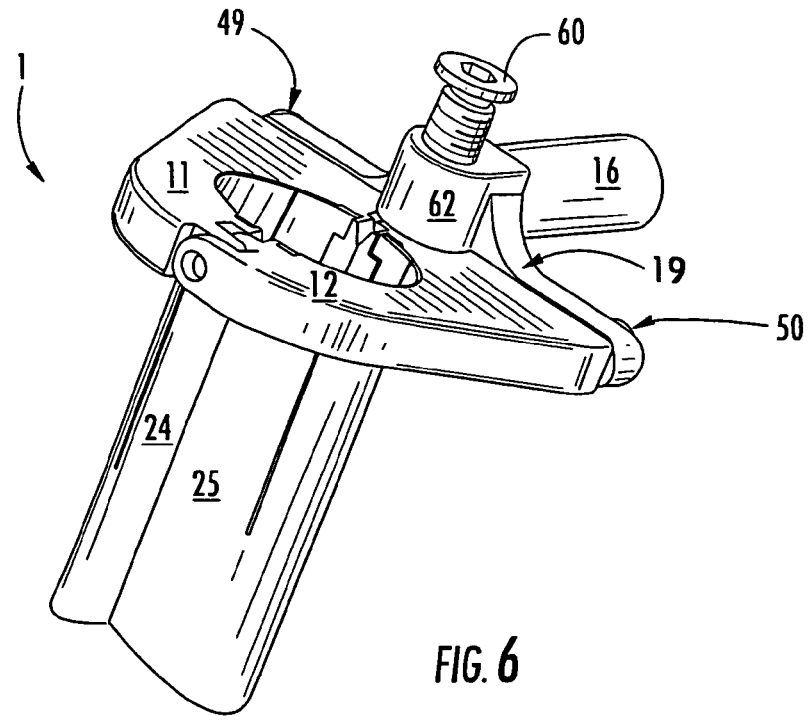
FIG. 6 is a perspective view of the retractor in the closed position.

FIG. 1 depicts one embodiment of the mount 10 with a first collar arm 11 and a second collar arm 12 rotatable around hinge axis 13. Collar arms 11 and 12 are rotatably connected to each other at forward hinge point 14 and rearward hinge point 15, and connected to frame 19 at first hinge 49 and second hinge 50. Specifically, first collar arm 11 is connected to frame 19 at first hinge 49 by a first hinge pin 52 that extends through a first slot 56 in frame 19. Similarly, second collar arm 12 is connected to frame 19 at second hinge 50 by a second hinge pin 54 that extends through a second slot 57 in frame 19. Hinge points 14 and 15, as well as hinges 49 and 50, allow for the rotational movement of collar arms 11 and 12. Additionally, slots 56 and 58 on frame 19 accommodate hinges 49 and 50, respectively, and allow for the horizontal translation of hinges 49 and 50 with respect to frame 19. Actuator 17 is oriented on frame 19 such that its rotational actuation causes it to translate distally (identified as DT in FIG. 7). Thus, as actuator 17 translates distally, it acts upon collar arms 11 and 12 causing the rotation of collar arms 11 and 12 around hinge axis 13, and causing hinge axis 13, itself, to translate distally. Rotation around hinge axis 13 is facilitated and accompanied by rotation of collar arms 11 and 12 around hinges 49 and 50, respectively, as well as translation of hinges 49 and 50 toward the center of frame 19 along slots 56 and 58, respectfully. All this motion, in turn, causes the expansion of the apparatus. Other actuating mechanisms for expanding and contracting the retractor 1 are also envisioned.

Mount channel 18 is oval in shape and located centrally between first and second collar arms 11 and 12. Mount channel 18 facilitates movement of instruments and other materials into and out of the surgical cavity created by the present invention. Mount channel 18 further comprises mount connection points 20, 21, 22, and 23 that allow for the connection between collar arms 11 and 12 and blades 24 and 25 (FIGS. 2,3, and 4).

FIGS. 2-5 show views of first blade 24, which is a mirror image of second blade 25 (shown in FIG. 6, for example). First blade 24 has a proximal end 26, a distal end 36, an inner portion 68 and a peripheral portion 70. Blade 24 also has blade connection points 27 and 28, hole 72, rearward slit 64 and forward slit 66. Additionally, as seen in FIGS. 3 and 4, the distal end 36 of blade 24 is tapered toward its periphery 70 to facilitate easier insertion through tissue.

Figure 13:
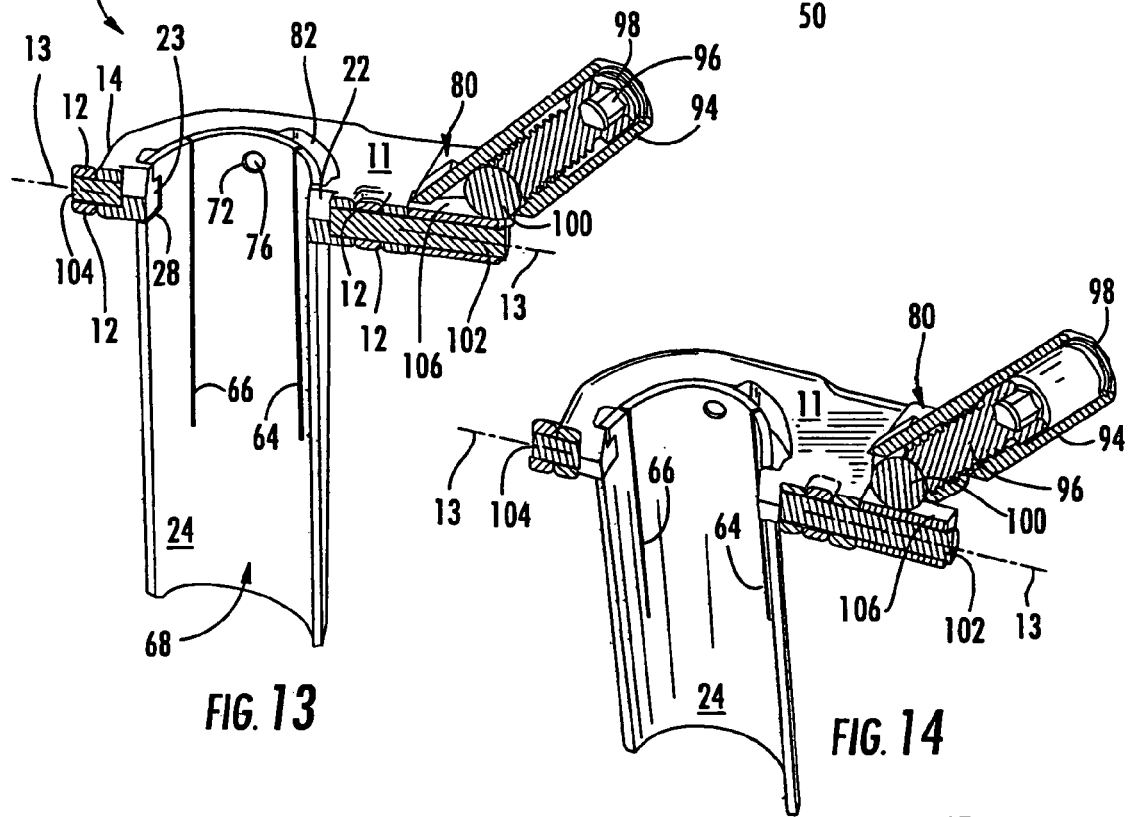
FIG. 13 is a perspective cut-away view of half of a retractor in the closed position with the mount of FIG. 12.
Figure 14:
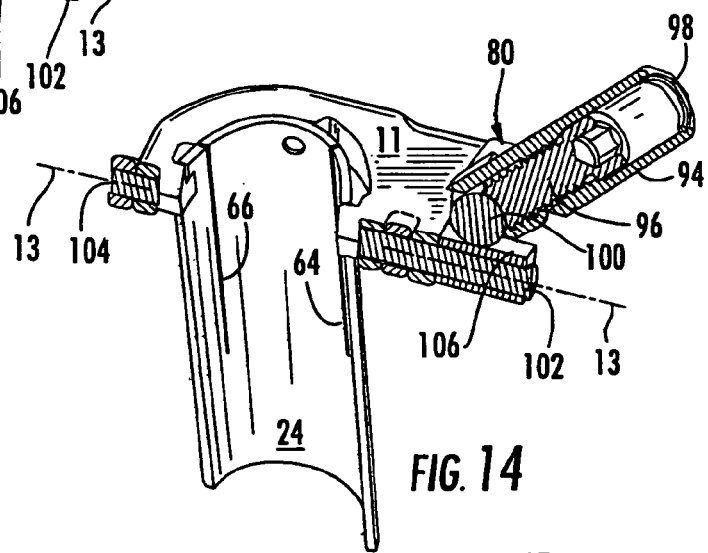
FIG. 14 is a perspective cut-away view of half of a retractor in the open position with the mount of FIG. 12.

As shown in assembled form in FIGS. 13 and 14, for example, proximal end 26 of blade 24 is connected at blade connection points 27 and 28, as well as at hole 72, to corresponding connection points 22 and 23, as well as pin 76, on first collar arm 11. Blade 24 gets connected to collar arm 11 by compressing proximal end 26, therefore moving blade connection points 27 and 28 toward each other, so as to prepare for assembly with connection points 22 and 23 on collar arm 11. Slits 64 and 66 facilitate this compression. It is recognized that compression of points 27 and 28 may be achieved by other configurations, and/or in other ways as well.

Once proximal end 26 is released from compression, blade 24 regains its original shape and firmly attaches to collar arm 11 through connections 27 to 22, 28 to 23, and 72 to 76. The male/female relationship of these connections, as well as the friction fit, allows the blade 24 to remain attached to the first collar arm 11 upon release of the compressive force that had been applied to the proximal end of blade 24.

Since first blade 24 is a mirror image of second blade 25, it is understood that the above description equally applies to the connection of second blade 25 to second collar arm 12. It is further recognized that many other connection configurations from the ones described above are possible. Such configurations may permit for interchangeability of blades 24 and 25, or just the removability of the blades for sterilization or disposability. Interchangeability allows a surgeon to readily change blades 24 and 25 depending upon, for example, the desired surgical cavity depth and/or cross-sectional area. Thus a surgeon may be provided with a kit of variably sized and shaped blades from which desired blades may be selected for a particular surgery or technique. Additionally, disposability of the blades allows for easier post-use handling techniques.

FIG. 5 shows a top view of first blade 24 where the blade's curvature is readily apparent. When placed together, blades 24 and 25 form a tube that is open at both the proximal and distal ends, with an oval channel therebetween. As shown in FIG. 6, this is the case when actuator 17 has not been translated distally and collar arms 11 and 12 have, therefore, not been rotated around hinge axis 13.

Figure 7:
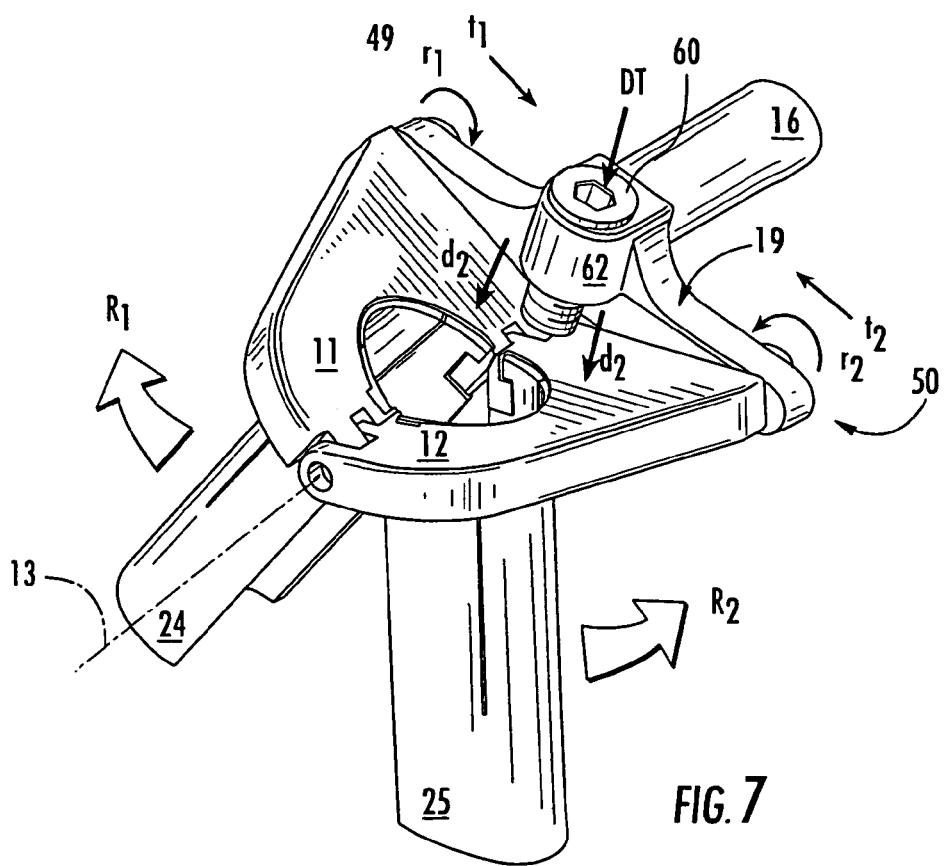
FIG. 7 is a perspective view of the retractor in the open position.

Actuator 17 comprises a screw 60 that is threadably assembled in housing 62, which is part of frame 19. As best seen in FIG. 7, in opening the retractor 1, upon distal translation DT of screw 60 through housing 62, collar arms 11 and 12 rotate around hinge axis 13 as hinge axis 13 is moved distally. In conjunction with this motion, first collar arm 11 rotates in direction $r_1$ around first hinge 49 as hinge 49 translates in direction $t_1$ in slot 56 (FIG. 1), and second collar arm 12 rotates in direction $r_2$ around second hinge 50 as hinge 50 translates in direction $t_2$ in slot 58 (FIG. 1). In this manner, blades 24 and 25 are displaced in respective retraction directions $R_1$ and $R_2$, and retractor 1 is opened. The displacement of blades 24 and 25 spreads apart tissue within the original incision and creates a larger surgical cavity, allowing for a larger working space for a surgeon. Additionally, as shown in FIGS. 3 and 6, for example, the distal ends 36 of blades 24 and 25 are tapered so as to allow easier insertion into the body of a patient.

It is recognized that the screw 60 may be engaged by a tool, such as screwdriver or an Allan key, to cause it to turn. Additionally, it is envisioned that multiple variations of the type of tool, interface with the screw, as well as screw types, or even the absence of a screw, are possible to accomplish moving the blades of the retractor towards and away from each other.

The material used in the construction of blades 24 and 25 is generally of a rigid type to support the spreading of the body tissue, such as aluminum, for example. In a preferred embodiment, the material is radiolucent or semi-radiolucent thereby allowing for the improved visualization of the anatomy when viewed on an X-ray with the retractor 1 in place. In other embodiments, the material may be non-autoclavable or otherwise non-sterilizable, and disposable. This further allows for the interchangeability of blades 24 and 25, to suit a particular surgical cavity.

FIG. 8 shows an embodiment of a sheath 29 of the present invention. Sheath 29 is preferably made of a pliable, elastic, and translucent material, such as silicone rubber, and fits snugly around blades 24 and 25. Preferably, sheath 29 is assembled over blades 24 and 25 when the retractor 1 is in the unexpanded condition, such as in FIG. 6. Upon distal translation DT of screw 60 of actuator 17, and displacement $R_1$ and $R_2$ of blades 24 and 25, sheath 29 stretches and forms an enclosure around blades 24 and 25, as shown in FIG. 9. This enclosure allows for a more manageable surgical cavity by preventing tissue from entering the cavity. Sheath 29 may also be made of a completely clear material, so that when in the expanded condition, a surgeon may see tissue and objects through sheath 29 when it is in the surgical cavity.

Preferably, to prevent sheath 29 from riding up on blades 24 and 25 during the opening of the retractor 1, the sheath 29 is sized slightly shorter than the length of the longest vertical peripheral dimension of blades 24 and 25, as seen in FIG. 3. In this configuration, when retractor 1 is opened, the distal end of sheath 29 stretches over and hooks onto the distal central edges of the blades 24 and 25, thus preventing the sheath's movement up the blades.

Upon the reverse translation of screw 60 and the return of blades 24 and 25 to their original state, sheath 29 returns to its original form as well. Depending on the pliability of the material used to construct sheath 29, the sheath may aid in bringing blades 24 and 25 back to their original, unexpanded condition. In any event, the tissue surrounding the blades 24 and 25 aids in compressing the blades back to their unexpanded condition. It should be noted that various materials with the above desirable properties for the sheath 29 may improve the cost-effectiveness of the sheath's 29 disposability. Additionally, the sheath 29 may be of any shape or size and may cover any area of the retractor 1, thereby creating any portion of covered and non-covered areas of blades 24 and 25.

FIG. 10 shows dilator assembly 30. This assembly is utilized prior to the introduction of retractor 1 into the body of the patient. Dilator assembly 30 includes guide 31 and increasingly sized dilators 32, 33, 34, and 35. Each of these dilators is a tube with an outside cross-section and an inside cross-section. The inside cross-section of each dilator is slightly larger than the outside cross-section of the next smallest dilator, while the outside cross-section of each dilator is slightly smaller than the inside cross-section of the next largest dilator. This allows for successive dilators to be placed over one another. Initially, guide 31 is inserted through an incision and secured within the body of a patient. Dilator 32 is then slid over guide 31 into the incision, thereby spreading the incision, and creating a surgical cavity having an area corresponding to the size of the dilator's outside cross-section. This step is repeated with successive dilators 33, 34, and 35 until the desired surgical cavity is achieved. It should be noted that any quantity of variously-sized dilators may be used to achieve this surgical cavity. Additionally, the dilators may be of any size or shape as long as they interact with one another as described above and allow the surgical cavity to be created and enlarged.

With reference to FIG. 11, subsequent to inserting all the desired dilators into the incision, retractor 1 is inserted over the largest dilator 35 in the cavity. This is done while blades 24 and 25 are together, whereby they form a passage extending distally from mount channel 18. This passage is large enough to accommodate the largest dilator 35 within it. Additionally, the tapered distal ends 36 of blades 24 and 25 facilitate easier insertion through the tissue.

Once retractor 1 is in place over the largest dilator 35, the guide 31 and all dilators 32-35 are removed from the surgical cavity. This leaves an opening corresponding to the passage extending from the proximal ends 26 to the distal ends 36 of the blades 24 and 25. Blades 24 and 25 of retractor 1 may then be expanded, thus enlarging the surgical cavity. It is also contemplated that retractor 1 may be inserted into the body in an orientation allowing blades 24 and 25 to displace in the same direction in which the muscles run in the area of the surgical site. Orienting retractor 1 in this fashion helps minimize muscle tissue damage and contributes to a faster recovery time from surgery for the patient. However, retractor 1 may be oriented in any fashion necessary to create a larger surgical cavity, in any area of the body. The introduction of retractor 1 into the body of a patient allows for the preservation of a small portal at the skin's surface.

Figure 12:
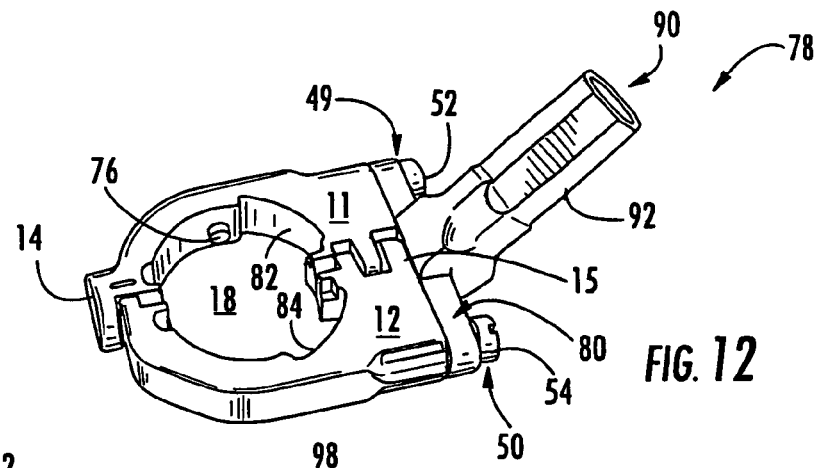
FIG. 12 is a perspective view of another embodiment of a mount portion of the retractor.

FIGS. 12-14 show another preferred embodiment of a retractor 2 of the present invention. This retractor 2 features a different frame 80 and actuator arrangement 90 from frame 19 and actuator 17 of retractor 1. Here, actuator 90 comprises a screw 96 threadably engaged in an actuator housing 94, and a ball 100 within the housing 94. The ball 100 rides on a bearing element 106 that resides on hinge pin 102. Hinge pin 102 couples the first and second collar arms 11 and 12 together at rearward hinge point 15, while hinge pin 104 couples collar arms 11 and 12 together at forward hinge point 14. Both hinge pins, 102 and 104, are on the same hinge axis 13. It is understood, however, that other variations are also possible.

The housing 94 is part of frame 80, but is oriented at an angle that is other than parallel to hinge axis 13. Additionally, the exterior 92 of housing 94 is shaped to serve the same function as retractor connection segment 16 of retractor 1, which is to facilitate coupling the retractor to a support structure that aids in maintaining the position of the retractor in place relative to the patient. The proximal interior of housing 92 contains a stop ring 98 which serves as a restriction to retraction of screw 96 beyond the proximal end of housing 94, to prevent screw 96 from being inadvertently removed from housing 94 during the closing of retractor 2.

Further, collar arms 11 and 12 also have cutouts 82 and 84, respectfully, which aid in attaching and removing blades 24 and 25 to collar arms 11 and 12, by providing additional manipulation space for the proximal ends 26 of blades 24 and 25.

FIGS. 13 and 14 show a cut-away view of half of retractor 2, where actuator 90, frame 80, first collar arm 11, and first blade 24 are visible. FIG. 13 shows retractor 2 in the closed position, while FIG. 14 shows retractor 2 in the open position.

Beginning with the closed arrangement of retractor 2 in FIG. 13, to expand the blades 24 and 25 of the retractor 2, screw 96 is advanced distally in housing 94. As screw 96 is advanced, it pushes on ball 100, which, in turn, pushes on bearing element 106. Bearing element 106 is coupled to hinge pin 102 which is part of rearward hinge point 15. Hinge pin 102 rotatably joins collar arms 11 and 12, and hinge point 15 is capable of moving distally. Thus, as screw 96 is advanced, ball 100 pushes downwardly on bearing element 106. Bearing element 106 then moves downwardly together with hinge pin 102, which causes hinge point 15 to move distally and, therefore, blades 24 and 25 to expand from the closed configuration in FIG. 13 to the open configuration in FIG. 14. The amount of distal movement of hinge point 15 is the same as the vertical component of the movement of ball 100 from its position in FIG. 13 to its position in FIG. 14. Thus, in opening the retractor 2, ball 100 moves from an elevated rearward position on bearing element 106, as shown in FIG. 13, to a lowered forward position on bearing element 106, as shown in FIG. 14.

Preferably, ball 100 is made of a ceramic material, and has a low-friction surface. The ceramic material is used for the resulting strength of the ball 100, while the low-friction surface is to diminish the undesirable friction forces associated with the functioning of actuator 90, which otherwise increase the effort required to open the retractor 2. Bearing element 106 and screw 96 may be made of any suitable material, and have any suitable surface finish, to compliment and improve the functionality and compatibility of the retractor 2, given the above parameters. For example, the tip of screw 96 that contacts ball 100, may have a low-friction surface to further diminish the frictional forces involved in advancing ball 100 along bearing element 106.

Figure 15:
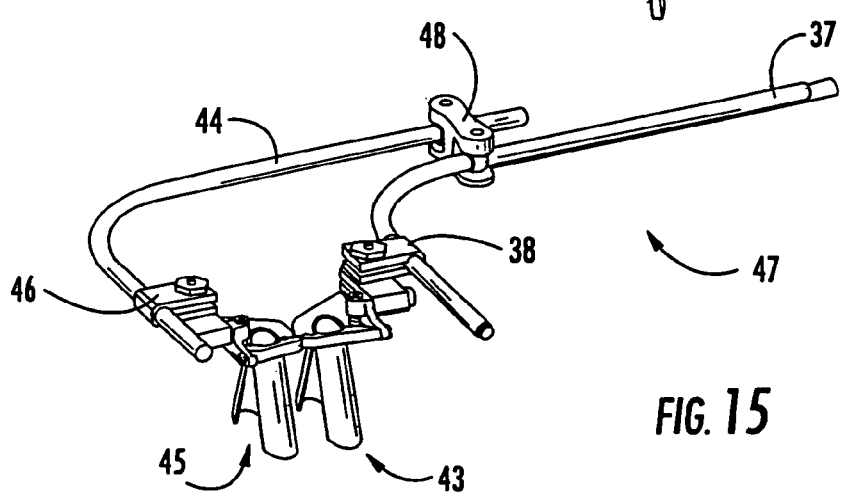
FIG. 15 is a perspective view of a surgery set-up including a frame assembly supporting two retractors.

FIG. 15 shows a typical configuration where one or more retractors are used in conjunction with a support assembly 47. The support assembly 47 comprises a first bar 37 connected to a first retractor 43 through a first holder 38. Optionally, there is a second bar 44 connected to a second retractor 45 through a second holder 46. The first and second bars are joined together at coupling 48. The support assembly 47 is ultimately attached to a rigid structure that facilitates maintaining the retractors 43 and 45 in relative position with respect to the patient.

An example of a support assembly of this type is the AF400 SpineTract System manufactured by Omni-Tract Surgical, a division of Minnesota Scientific. However, different support assemblies can be used, including but not limited to single support assemblies, where only one retractor is utilized.

It is further contemplated that the retractor of the present invention may be utilized on any part of the patient where a small incision but large subcutaneous operating area is desirable.

It is also contemplated that objects including but not limited to surgical instruments, surgical implants, and connection devices can be introduced into the body of a patient through the retractor of the present invention. The methods of use, as described above, may be performed with one or more retractors, with or without support assemblies, and in sequences different from those described. Additionally, the steps utilizing dilators may or may not be performed. Alternatively, various quantities, sizes, or shapes of dilators may be utilized. Finally, the present invention may be a kit encompassing the various elements disclosed above. This kit may include, but is not limited to, differently sized and shaped mounts 10, blades 24 and 25, and sheaths 29. Any or all of these different elements may be interchanged to suit the desired surgical cavity. Depending upon the conditions, a surgeon may select different mounts 10, blades 24 and 25, and sheaths 29 for assembly and use.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A retractor comprising:
a frame;
a first collar arm and a second collar arm;
an actuator adapted to cause simultaneous motion of said first collar arm and said second collar arm; and
a first blade and a second blade, each having a proximal end, and a distal end;
wherein
at least a portion of said actuator is part of said frame;
said first blade is connected to said first collar arm;
said second blade is connected to said second collar arm;
said first and said second collar arms are each pivotally and translationally coupled to said frame; and
said retractor has
an unexpanded position defined by said distal end of said first blade being closer to said distal end of said second blade; and
an expanded position defined by said distal end of said first blade being farther away from said distal end of said second blade.

2. The retractor of claim 1, further comprising an elastic sheath at least partially surrounding said first and said second blades.

3. The retractor of claim 2, wherein when said retractor is in said expanded position, said elastic sheath circumferentially encloses a passage between said first and said second blades.

4. The retractor of claim 1, wherein said first collar arm is pivotally connected to said second collar arm.

5. The retractor of claim 4, wherein said first collar arm is pivotally connected to said second collar arm through a coupling having a hinge axis formed therethrough, said first and second collar arms being pivotable about said hinge axis.

6. The retractor of claim 5, wherein said hinge axis is adapted to move distally with respect to said frame.

7. The retractor of claim 1, wherein said first collar arm is connected to said proximal end of said first blade, and said second collar arm is connected to said proximal end of said second blade.

8. The retractor of claim 2, wherein said elastic sheath is at least partially transparent or translucent.

9. The retractor of claim 1, wherein said actuator is adapted to move said retractor from said unexpanded position to said expanded position.

10. The retractor of claim 1, wherein said actuator comprises a screw in a housing.

11. The retractor of claim 10, wherein said housing is part of said frame, and wherein said actuator is adapted to move said retractor from said unexpanded position to said expanded position.

12. The retractor of claim 1, wherein said distal ends of said first and said second blades are tapered.

13. The retractor of claim 1, wherein said first and second blades are detachable from said first and second collar arms.

14. The retractor of claim 1, wherein said first collar arm is pivotally and translationally coupled to said frame by a first pin extending through a first slot, and wherein said second collar arm is pivotally and translationally coupled to said frame by a second pin extending through a second slot.

15. A retractor comprising:
a frame having a middle portion and first and second outer ends;
a first collar arm and a second collar arm, each having a top side, a bottom side, an outer portion and a central portion; and a first blade and a second blade, each having a proximal end, a distal end, a peripheral portion and an inner portion; wherein said outer portion of said first collar arm is pivotally and translationally coupled to said frame;

said outer portion of said second collar arm is pivotally and translationally coupled to said frame;

said central portion of said first collar arm is rotatably coupled to said central portion of said second collar arm through a coupling such that a hinge axis is formed through said coupling;

said proximal end of said first blade is connected to said first collar arm;

said proximal end of said second blade is connected to said second collar arm;

and wherein said hinge axis is adapted to move distally while said outer portions of said first and second collar arms translate toward said middle portion of said frame and rotate with respect to said frame, in order to facilitate increasing a distance between said distal ends of said first and second blades.

16. The retractor of claim 15, further comprising an actuator adapted to move said hinge axis distally.

17. The retractor of claim 16, wherein said actuator comprises a screw rotatably arranged in a housing.

18. The retractor of claim 15, wherein said first and second blades are detachable from said first and second collar arms.

19. The retractor of claim 15, wherein said outer portion of said first collar arm is pivotally and translationally coupled to said frame by a first pin extending through a first slot, and wherein said outer portion of said second collar arm is pivotally and translationally coupled to said frame by a second pin extending through a second slot.

* * * * *